United States Patent [19]
Afriat et al.

[11] Patent Number: 5,935,588
[45] Date of Patent: Aug. 10, 1999

[54] STABLE W/O/W EMULSION CONTAINING A WATER-SENSITIVE COSMETIC AND/OR DERMATOLOGICAL ACTIVE AGENT

[75] Inventors: Isabelle Afriat, Paris; Didier Gagnebien, Chatillon, both of France

[73] Assignee: L'Oreal, Paris, France

[21] Appl. No.: 08/915,469

[22] Filed: Aug. 20, 1997

Related U.S. Application Data

[63] Continuation of application No. 08/767,283, Dec. 16, 1996.

[30] Foreign Application Priority Data

Dec. 15, 1995 [FR] France .................................. 95 14940

[51] Int. Cl.$^6$ ............................... A61K 6/00; A61K 7/00; A61K 31/74
[52] U.S. Cl. .................... 424/401; 424/70.12; 424/78.03
[58] Field of Search .............................. 424/70.12, 78.03, 424/401; 514/937

[56] References Cited

U.S. PATENT DOCUMENTS 5,567,426  10/1996  Nadaud ..................................... 424/401

*Primary Examiner*—Thurman K. Page
*Assistant Examiner*—Sharon Howard
*Attorney, Agent, or Firm*—Oblon, Spivak, McClelland, Maier & Neustadt, P.C.

[57] ABSTRACT

A water/oil/water triple emulsion containing an outer aqueous phase and an oil phase constituting, with an inner aqueous phase, a W/O primary emulsion, one of the aqueous phases of the triple emulsion having a water activity value of less than or equal to 0.85, in particular for the purpose of stabilizing a water-sensitive active agent contained in the aqueous phase with low water activity, which emulsion obtained can constitute a composition for cleansing and/or caring for and/or protecting the skin and/or mucous membranes and/or keratinous fibres.

26 Claims, No Drawings

STABLE W/O/W EMULSION CONTAINING A WATER-SENSITIVE COSMETIC AND/OR DERMATOLOGICAL ACTIVE AGENT

This application is a Rule 53 Continuation of U.S. Ser. No. 08/767,283, filed Dec. 16, 1996.

BACKGROUND OF THE INVENTION

1. Field of the Invention

The present invention relates to a stable medium capable of containing a water-sensitive active agent which can be used in particular in the cosmetic and/or dermatological fields for cleansing and/or caring for and/or protecting the skin and/or mucous membranes and/or keratinous fibres.

2. Description of the Background

It is known to introduce active agents into cosmetic and/or dermatological compositions for the purpose of contributing specific treatments to the skin and/or hair, for example for cleansing the skin, for controlling drying, ageing or pigmentation of the skin, for treating acne or certain skin diseases (eczema, psoriasis), for combating excess weight, for promoting restructuring of the skin or its cell renewal or for treating seborrhoea of the hair.

For example it is known to introduce, into cosmetic compositions, enzymes and in particular proteases used for their proteolytic properties. These enzymes are sought after in the cosmetics field for their smoothing and cleansing power and their ability to remove dead cells from the skin.

Unfortunately, some active agents, and in particular those mentioned above, have the disadvantage of being unstable in aqueous medium and of being readily degraded or modified under the influence of water. Thus they rapidly lose their activity over time, and this instability goes against the desired efficacy.

Various means have therefore been envisaged for overcoming this disadvantage. In particular, the incorporation of an active agent, in particular an enzyme, in a pulverulent composition has been envisaged (see JP-A-63-130514). Moreover, the majority of skin cleansing products containing an enzyme are provided in this form. It has also been envisaged to use these active agents, and in particular enzymes, in a form immobilized on polymeric supports (see JP-A-61-207499) or in microcapsules (see JP-A-61-254244). Unfortunately, some of these means necessitate a special procedure, which increases the cost and time associated with the preparation of the composition.

Another solution consists in incorporating them into an anhydrous liquid medium (see U.S. Pat. No. 5,322,683). Unfortunately, this solution limits the pharmaceutical form of the composition and does not permit the incorporation of hydrophilic active agents.

There is therefore still a need for a stable medium capable of containing water-sensitive hydrophilic and/or lipophilic cosmetic and/or dermatological active agents in which the latter would retain all their properties and thus their efficacy over time.

SUMMARY OF THE INVENTION

Applicants have now found, unexpectedly, that a water/oil/water (W/O/W) triple emulsion, one of the aqueous phases of which has a water activity value of less than or equal to 0.85, was capable of maintaining the activity of a watersensitive active agent and of preventing the degradation of the active agent.

The subject of the present invention is consequently a water/oil/water triple emulsion containing an outer aqueous phase and an oily phase constituting, with an inner aqueous phase, a water/oil primary emulsion, wherein one of the aqueous phases has a water activity value of less than or equal to 0.85.

DETAILED DESCRIPTION OF THE INVENTION

According to a specific embodiment of the invention, the water activity value of less than or equal to 0.85 is obtained by incorporation of an effective amount of polyol. Effective amount is understood to mean an amount of polyol which is sufficient to produce a low water activity value, that is to say a water activity value of less than or equal to 0.85.

Moreover, according to a preferred embodiment of the invention, the oily phase of the triple emulsion according to the invention contains at least one silicone oil and one silicone emulsifier.

This emulsion can advantageously be used as a vehicle for a water-sensitive active agent. The latter is introduced into the aqueous phase exhibiting a low water activity value. A further subject of the invention is consequently a composition, wherein it contains an emulsion as defined above and at least one water-sensitive active agent with a topical effect contained in the aqueous phase exhibiting a water activity value of less than or equal to 0.85.

It is certainly known to use, in the cosmetic and dermatological fields, water/oil/water emulsions in which one of the aqueous phases contains polyols. The reference WO-A-94/1073 thus discloses compositions of this type but it does not teach the introduction of a large amount of polyols, in particular for the purpose of stabilizing the water-sensitive active agents. In addition, it neither teaches nor suggests the presence of an aqueous phase having a low water activity.

Moreover, it is known that the water content can have an influence on the stability of water-sensitive active agents, but it has never been described nor suggested that the presence alone of polyol might prevent the degradation of such active agents. Thus, the reference D. Tzanos (Behavior of enzymes by controlling the medium water activity; Riv. Ital. Essenze, Profumi, Piante Off., Aromi, Saponi, Cosmet., Aerosol, 1977, vol. 59, No. 5, pages 208–211) encourages the person skilled in the art to use surfactants for stabilizing the enzymes in aqueous medium or to attach the enzymes to a porous support. In contrast, it leads the person skilled in the art away from using glycols.

Moreover, U.S. Pat. No. 5,356,800 describes a process for stabilizing enzymes which consists in using a mixture comprising an alcohol or a glycol, an oxyethylenated alkyldiamine and an amine oxide. According to this reference, the enzymes can only be stabilized by using the mixture described.

In addition, JP-A-01-283213 describes a cleansing composition containing an enzyme and a polyol. According to this reference, the enzymatic activity is stabilized by addition of a protein such as collagen, elastin or albumin.

It has now been found that the degradation of such active agents can be avoided by introducing them into the W/O/W emulsion according to the invention.

The triple emulsion according to the invention has the advantage not only of preserving the activity of the water-sensitive active agents but also of nevertheless transporting a sufficient amount of water due to the presence of water in the aqueous phase which does not have a reduced water activity. This presence of water makes it possible simultaneously to contribute water to the skin and to activate the enzyme at the time of application to the skin.

According to a preferred embodiment of the invention, the amount of the polyol or polyols must be such that the water activity value of one of the aqueous phases of the emulsion is less than or equal to 0.75.

The water activity $a_w$ of a medium containing water is the ratio of the water vapour pressure of the medium "$P_{H2O}$ medium" to the vapour pressure of pure water "$P_{H2O}$ pure" at the same temperature. It can also be expressed as the ratio of the number of molecules of water "$N_{H2O}$" to the total number of molecules "$N_{H2O}+N_{dissolved\ substances}$", which takes into account the molecules of dissolved substances "$N_{dissolved\ substances}$".

It is given by the following formulae:

$$a_w = \frac{P_{H2O}\ \text{medium}}{P_{H2O}\ \text{pure}} = \frac{N_{H2O}}{N_{H2O} + N_{dissolved\ substances}}.$$

Various methods can be used for measuring the water activity. The most common is the manometric method, by which the vapour pressure is measured directly.

Conventionally, a cosmetic or dermatological composition has a water activity of around 0.95 to 0.99. A water activity of less than 0.85 represents a considerable reduction in the water activity.

In the emulsion according to the invention, one or other of the aqueous phases (inner or outer) can exhibit a low water activity but it is preferably the continuous outer aqueous phase.

In order to have such a water activity of less than 0.85, the amount of polyol in the phase under-consideration must range from 35 to 90% by weight and better still from 60 to 85% by weight with respect to the total weight of the aqueous phase with a low water activity, that is to say be greater than 30% by weight with respect to the total weight of the emulsion and preferably range from 35 to 70% by weight with respect to the total weight of the emulsion.

The polyol used according to the invention can in particular be chosen from glycerol and glycols, in particular propylene glycol and polyethylene glycols.

According to a preferred embodiment of the invention, the polyol or polyols are totally or partially present in a form complexed with an acrylic or methacrylic polymer. The polymer may also comprise bound water, i.e. be complexed with a mixture of water and polyol(s).

Acrylic or methacrylic polymer is understood to mean a homopolymer or a copolymer of acrylic or methacrylic acid or a homopolymer or a copolymer of a derivative of acrylic or methacrylic acid.

The amount of such polymers with the complexed polyol or polyols and optionally complexed water in the emulsion according to the invention preferably ranges from 52 to 90% by weight and more preferably from 60 to 85% by weight with respect to the total weight of the aqueous phase with low water activity.

Homopolymers which complex water and polyols include those sold under the names Norgel and Lubrajel CG by the company Guardian. These polymers are poly(glyceryl acrylate)s complexed with more than 65% of glycerol and/or of propylene glycol and less than 35% by weight of water. These polymers provide the complexed polyol and the complexed water and may additionally act as gelling agent for the composition.

The water-sensitive active agents which can be used according to the invention are in particular enzymes (for example lactoperoxidase, lipase, protease, phospholipase or cellulases), natural extracts, such as green tea, balm extract, thyme extract, procyanidol oligomers (PCO), such as hawthorn PCO, pine PCO and grape PCO, vitamins and in particular ascorbic acid (vitamin C) and its esters or retinol (vitamin A) and its esters, phosphated and glucosylated derivatives, urea and rutin.

The water-sensitive active agent or agents used are advantageously an enzyme and more particularly a protease. This protease can be chosen, for example, from those sold under the trade names "Subtilisine SP 544", "Subtilisine SP 554" and "Subtilisine SP 582" by the company Novo Nordisk and that sold under the trade name "Lysoveg" by the company Laboratoires Seriobiologiques de Nancy.

The amount of water-sensitive active agent in the composition according to the invention depends on the type of active agent used. Generally, the active agent or agents can be used in the composition according to the invention in an amount ranging from 0.001 to 15% by weight, preferably from 0.01 to 10% and more preferably from 0.05 to 5% by weight with respect to the total weight of the composition.

To provide for the emulsification of the primary emulsion in the continuous outer aqueous phase of the emulsion, it contains a polymer of emulsifying nature, in particular a polymer with a fatty chain of the $C_3$–$C_6$ monoethylenic carboxylic acid anhydride or acid/acrylic ester with a fatty chain copolymer type. This polymer with a fatty chain can be chosen in particular from the copolymers sold under the names "Pemulen" and "Carbopol 1342" or "Carbopol 1382" by the company Goodrich. The amount of such polymers in the emulsion according to the invention can preferably range from 0.05 to 3% by weight with respect to the total weight of the emulsion.

The continuous outer aqueous phase can in addition contain one or a number of gelling agents, for example a carboxyvinyl polymer, such as those sold under the names "Carbopol 980" or "Carbopol 942" or "Carbopol 950" by the company Goodrich or that sold under the name "Synthalen K" by the company Sigma. The amount of such gelling agents in the emulsion according to the invention can preferably range from 0.05 to 3% by weight with respect to the total weight of the emulsion.

Advantageously, the oily phase is essentially composed of at least one silicone emulsifier and one silicone oil.

The silicone emulsifiers can be chosen from dimethicone copolyols and alkyldimethicone copolyols. Emulsifiers which can be used in the emulsion according to the invention include the Polyglyceryl-4 isostearate/Cetyl dimethicone copolyol/Hexyl laurate mixture sold under the name "Abil WE 09" by the company Goldschmidt, Cetyl dimethicone copolyol sold under the name "Abil EM 90" by the company Goldschmidt and the cyclomethicone/dimethicone copolyol mixture sold under the name "Q2-3225C" by the company Dow Corning. The amount of silicone emulsifier in the emulsion according to the invention preferably ranges from 0.05 to 10% by weight and preferably from 0.5 to 8% by weight with respect to the total weight of the triple emulsion.

The silicone oils can be chosen, for example, from volatile silicones, such as cyclopentadimethyl-siloxane and cyclotetradimethylsiloxane, polydimethyl-siloxanes, polyphenyltrimethylsiloxanes or fluorinated silicones. The amount of silicone oils ranges from 0.5 to 60% by weight and preferably from 10 to 30% by weight with respect to the total weight of the triple emulsion.

The emulsion according to the invention can in addition comprise one or a number of other fatty substances chosen from silicone waxes, gums or resins and optionally non-silicone oils. These fatty substances can be used, for example, in an amount ranging from 0.05 to 5% by weight with respect to the total weight of the triple emulsion.

Use may in particular be made, as waxes, of silicone waxes, such as alkoxydimethylsiloxanes and more particularly stearoxypolydimethylsiloxanes, alkylpolysiloxanes and polydimethylsiloxanes containing mercapto functional groups.

Use may in particular be made, as gums, of silicone gums, such as high molecular weight polydimethylsiloxanes or polydimethylsiloxanes with hydroxyl endings (dimethiconols).

Use may in particular be made, as resins, of silicone resins, such as trimethylsiloxysilicates.

Non-silicone oils include fluorinated oils, oils of animal or vegetable origin, mineral oils and synthetic oils.

The primary emulsion can represent, for example, from 10 to 40% by weight with respect to the total weight of the triple emulsion.

According to a specific embodiment of the invention, the primary emulsion constitutes from 20 to 35% and more particularly 25% by weight of the triple emulsion, which makes it possible to obtain a translucent or transparent triple emulsion.

The triple emulsion is prepared conventionally by preparation of the primary emulsion and incorporation of a predetermined amount of the primary emulsion in the outer aqueous phase.

According to a specific embodiment of the invention, the primary emulsion contains a portion of the silicone oil, for example at most 20% by weight with respect to the total weight of the primary emulsion, and the remainder of the silicone oil is then added to the amount of primary emulsion used to prepare the triple emulsion, before adding the mixture to the outer aqueous phase.

For a topical application, the emulsion according to the invention must contain a medium which is topically acceptable, that is to say compatible with the skin and hair, and the composition based on this emulsion can in particular constitute compositions for cleansing, protection, treatment or care of the skin and/or hair, in particular for the face, neck, hands, hair, scalp or body, as well as for the eyelashes.

A further subject of the invention is consequently the use of the composition according to the invention for cleansing and/or protecting the skin and/or mucous membranes and/or keratinous fibres, that is to say the hair and/or eyelashes.

Another subject of the invention is a cosmetic and/or dermatological process for cleansing and/or protecting the skin and/or mucous membranes and/or keratinous fibres, wherein it comprises the application to the skin and/or mucous membranes and/or keratinous fibres of a composition as defined above.

A final subject of the present invention is a cleansing composition for the skin and/or keratinous fibres, wherein it contains an emulsion as defined above and at least one water-sensitive active agent with a topical effect contained in the aqueous phase exhibiting a water activity value of less than or equal to 0.85.

The composition according to the invention can in particular constitute creams for the protection, treatment or care of the face, hands or feet, body milks for protection or care, or lotions, gels or mousses for the care of the skin, mucous membranes, hair and scalp.

In a known way, the composition of the invention may also contain adjuvants usual in the cosmetics and dermatological fields, such as surfactants, in particular foaming surfactants, hydrophilic or lipophilic active agents, in addition to the watersensitive active agents, preservatives, antioxidants, solvents, fragrances, fillers, screening agents, odour absorbers, colouring materials and lipid vesicles. The amounts of these various adjuvants are those conventionally used in the fields under consideration and are, for example, from 0.01% to 15% of the total weight of the composition. These adjuvants, depending on their nature, can be introduced into the fatty phase or into the aqueous phase.

Use may be made, as hydrophilic active agents, of, for example, proteins or protein hydrolysates, amino acids, allantoin, sugars and sugar derivatives, or starch.

Use may be made, as lipophilic active agents, of, for example, tocopherol (vitamin E) and its derivatives, essential fatty acids, ceramides or essential oils.

Having generally described this invention, a further understanding can be obtained by reference to certain specific examples which are provided herein for purposes of illustration only and are not intended to be limiting unless otherwise specified.

The examples below of compositions according to the invention are given by way of illustration and without limiting nature. The amounts therein are given in % by weight.

EXAMPLE 1

Triple emulsion for smoothing the face primary emulsion (W/O):

| Oily phase: | |
| --- | --- |
| Abil WE-09, sold by the company Goldschmidt | 2.5% |
| Polydimethylsiloxane | 4% |
| Cyclopentadimethylsiloxane | 17.5% |
| Aqueous phase: | |
| Magnesium sulphate | 0.8% |
| Preservative | 0.2% |
| Glycerol | 2% |
| Propylene glycol | 20% |
| Water | 53% |
| Triple emulsion: | |
| Primary emulsion | 25% |
| Cyclopentadimethylsiloxane | 10% |
| Subtilisine SP544 | 0.1% |
| Carbopol 1342 | 0.3% |
| Triethanolamine | 0.3% |
| Norgel containing 67.8% of glycerol | 52.7% |
| Water | 11.6% |

The procedure for preparing the emulsion is as follows:

The primary emulsion is prepared by emulsifying the aqueous phase in the oily phase by homogenization using a propeller. 25% of the primary emulsion obtained are taken and 10% of cyclopentadimethylsiloxane are added thereto. Moreover, the outer aqueous phase is prepared by incorporating 10% of a 3% aqueous Carbopol 1342 solution in the Norgel. The primary emulsion is then emulsified in the outer aqueous phase with vigorous stirring; triethanolamine is then added and finally Subtilisine SP544.

The water activity of the outer phase of this emulsion is 0.77±0.02.

A transparent cream is obtained which is capable of smoothing the skin and rendering it uniform.

EXAMPLE 2
Triple emulsion for moisturizing the skin

| Primary emulsion (W/O): | |
|---|---|
| Oily phase: | |
| Abil WE-09 sold by the company Goldschmidt | 2.5% |
| Polydimethylsiloxane | 4% |
| Cyclopentadimethylsiloxane | 17.5% |
| Aqueous phase: | |
| Magnesium sulphate | 0.8% |
| Glycerol | 51% |
| Propylene glycol | 20% |
| Water | 4.1% |
| Subtilisine SP554 | 0.1% |
| Triple emulsion: | |
| Primary emulsion | 20% |
| Cyclopentadimethylsiloxane | 10% |
| Carbopol 980 gel containing I % of A.M. | 30% |
| Preservatives | 1% |
| Carbopol 1382 | 0.3% |
| Triethanolamine | 0.3% |
| Water | 38.4% |

The procedure for preparing the emulsion is as follows:

The primary emulsion is prepared by emulsifying the aqueous phase containing the Subtilisine SP554 in the oily phase by homogenization using a propeller. 10% of cyclopentadimethylsiloxane are added to 20% of the primary emulsion thus obtained. Moreover, the Carbopol 980 gel is prepared by mixing 1% of Carbopol 980 with 1% of triethanolamine and 98% of water. The outer aqueous phase is prepared by mixing this gel with the remainder of the constituents, except the triethanolamine. The primary emulsion is then emulsified in the outer aqueous phase with vigorous stirring and the triethanolamine is added.

The water activity of the aqueous phase of the primary emulsion is 0.22.

A white cream is obtained which is capable of moisturizing the skin.

In the above examples, the Subtilisine could be replaced according to the invention by other enzymes, ascorbic acid, green tea and the other water-sensitive active agents mentioned above.

The disclosure of French priority application 95-14940, filed Dec. 15, 1995, is hereby incorporated by reference.

Obviously, numerous modificatiors and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. Water/oil/water triple emulsion containing an outer aqueous phase and an oily phase together with an inner aqueous phase in the form of a water/oil primary emulsion, wherein one of the aqueous phases has a water activity value of less than or equal to 0.85 containing a polyol in an amount ranging from 35 to 90% by weight with respect to the total weight of the aqueous phase.

2. Water/oil/water triple emulsion according to claim 1, wherein the oily phase comprises at least one silicone oil and one silicone emulsifier.

3. Water/oil/water triple emulsion according to claim 1, wherein the aqueous phase having a water activity of less than or equal to 0.85 is the outer aqueous phase.

4. Water/oil/water triple emulsion according to claim 1, wherein the aqueous phase having a water activity value of less than or equal to 0.85 comprises at least one polyol in an amount which is effective in producing a water activity value of the said phase which is less than or equal to 0.75.

5. Water/oil/water triple emulsion according to claim 1, wherein the polyol is present in the aqueous phase having a water activity of less than or equal to 0.85 in an amount ranging from 35 to 70% by weight with respect to the total weight of the emulsion.

6. Water/oil/water triple emulsion according to claim 1, wherein the polyol is selected from the group consisting of glycerol and glycols.

7. Water/oil/water triple emulsion according to claim 1, wherein the polyol is complexed with an acrylic or methacrylic polymer.

8. Water/oil/water triple emulsion according to claim 7, wherein the polymer additionally comprises (bound water complexed, therein.

9. Water/oil/water triple emulsion according to claim 8, wherein the polymer with the complexed polyol and the complexed water is present in an amount ranging from 52 to 90% by weight with respect to the total weight of the aqueous phase having a water activity of less than or equal to 0.85.

10. Water/oil/water triple emulsion according to claim 1, wherein the outer aqueous phase of the triple emulsion comprises a polymer with a fatty chain.

11. Water/oil/water triple emulsion according to claim 10, wherein the polymer with a fatty chain is a $C_3$–$C_6$ monoethylenic carboxylic acid anhydride or acid/acrylic ester with a fatty chain copolymer.

12. Water/oil/water triple emulsion according to claim 11, wherein the polymer with a fatty chain represents from 0.05 to 3% by weight with respect to the total weight of the emulsion.

13. Water/oil/water triple emulsion according to claim 3, wherein the oily phase comprises at least one silicone oil in an amount ranging from 0.5 to 60% by weight with respect to the total weight of the triple emulsion.

14. Water/oil/water triple emulsion according to claim 13, wherein the silicone oil is selected from the group consisting of volatile silicones, polydimethylsiloxanes, polyphenyltrimethylsiloxanes and fluorinated silicones.

15. Water/oil/water triple emulsion according to claim 3, wherein the emulsifier is selected from the group consisting of alkyldimethicone copolyols and dimethicone copolyols.

16. Water/oil/water triple emulsion according to claim 3, wherein the emulsifier is present in an amount ranging from 0.05 to 10% by weight with respect to the total weight of the emulsion.

17. Water/oil/water triple emulsion according to claim 1, wherein the oily phase additionally contains one or a number of other fatty substances selected from the group consisting of silicone waxes, gums or resins and non-silicone oils.

18. Water/oil/water triple emulsion according to claim 1, wherein the water/oil primary emulsion represents 20 to 35% by weight with respect to the total weight of the emulsion.

19. Water/oil/water triple emulsion according to claim 1, wherein the emulsion is transparent.

20. A composition containing an emulsion according to claim 1, wherein at least one water-sensitive active agent with a topical effect is contained in the aqueous phase having a water activity value of less than or equal to 0.85.

21. A composition according to claim 20, wherein the water-sensitive active agent is selected from the group consisting of enzymes, natural extracts, procyanidol oligomers, vitamins, phosphated and glucosylated derivatives, urea and rutin.

22. A composition according to claim 20, wherein the water-sensitive active agent is selected from the group consisting of a protease, green tea, ascorbic acid and vitamin A.

23. A composition according to claim 22, wherein the water-sensitive active agent is present in a concentration ranging from 0.001 to 15% by weight with respect to the total weight of the emulsion.

24. A composition according to claim 22, having a cosmetic and/or dermatological activity.

25. A composition according to claim 22, additionally containing at least one lipophilic or hydrophilic adjuvant selected from the group consisting of preservatives, antioxidants, fragrances, fillers, screening agents, sequestering agents, essential oils, colouring materials, hydrophilic or lipophilic active agents and lipid vesicles.

26. A method for cleansing and/or protecting a substrate selected from the group consisting of the skin, mucous membranes and keratinous fibres comprising applying the composition of claim 22 to said substrate.

* * * * *